United States Patent
Nelson et al.

(10) Patent No.: US 6,777,120 B2
(45) Date of Patent: Aug. 17, 2004

(54) RELATIVE HUMIDITY SENSOR WITH COMPENSATION FOR CHANGES IN PRESSURE AND GAS COMPOSITION

(75) Inventors: Patricia J. Nelson, Rochester, NY (US); Jameson R. Forte, Webster, NY (US); Eric L. Thompson, Honeoye Falls, NY (US)

(73) Assignee: General Motors Corporation, Detroit, MI (US)

( * ) Notice: Subject to any disclaimer, the term of this patent is extended or adjusted under 35 U.S.C. 154(b) by 305 days.

(21) Appl. No.: 09/863,715

(22) Filed: May 23, 2001

(65) Prior Publication Data

US 2002/0177017 A1 Nov. 28, 2002

(51) Int. Cl.[7] .............................. H01M 8/04; H01M 8/12
(52) U.S. Cl. .............................. 429/22; 429/24; 429/25
(58) Field of Search .............................. 429/22, 24, 25, 429/13, 17; 73/25.01, 25.04, 29.01, 29.03; 236/44 R, 44 A, 44 C

(56) References Cited

U.S. PATENT DOCUMENTS

| | | | |
|---|---|---|---|
| 3,719,529 A | * | 3/1973 | Lake ........................... 205/783 |
| 5,190,726 A | * | 3/1993 | Shinoki et al. ................ 422/62 |
| 5,712,052 A | * | 1/1998 | Kawatsu ....................... 429/13 |
| 5,935,725 A | | 8/1999 | Dhar et al. |
| 5,952,119 A | | 9/1999 | Wilson |
| 6,013,385 A | * | 1/2000 | DuBose ....................... 429/17 |

FOREIGN PATENT DOCUMENTS

JP  62-176064  * 8/1987 ............ H01M/8/04

* cited by examiner

Primary Examiner—Patrick Ryan
Assistant Examiner—Julian Mercado
(74) Attorney, Agent, or Firm—Cary W. Brooks; Linda M. Deschere

(57) ABSTRACT

A sensor system for sensing the relative humidity level of gas stream in a fuel cell includes a humidity sensor that senses the relative humidity of a gas stream and generates a relative humidity signal. A pressure sensor senses the pressure of the gas stream and generates a pressure signal. A temperature sensor senses the temperature of the gas stream and generates a temperature signal. A compensator is connected to the humidity sensor, the temperature sensor and/or the pressure sensor. The compensator generates a compensated relative humidity signal based on the relative humidity signal, the temperature signal and/or the pressure signal. Additional inputs to the compensator can include one or more gas composition sensors that determine the concentration of one or more gases.

20 Claims, 3 Drawing Sheets

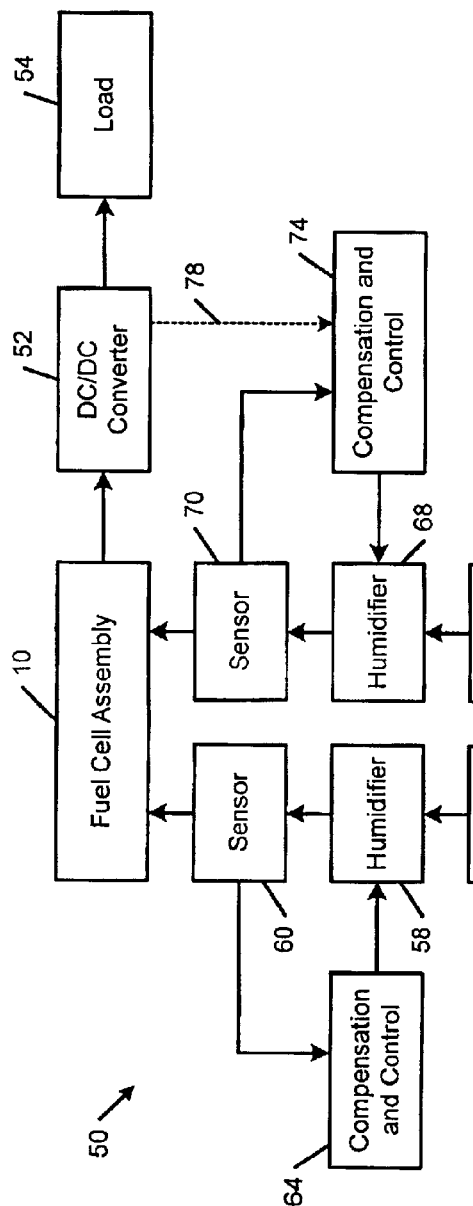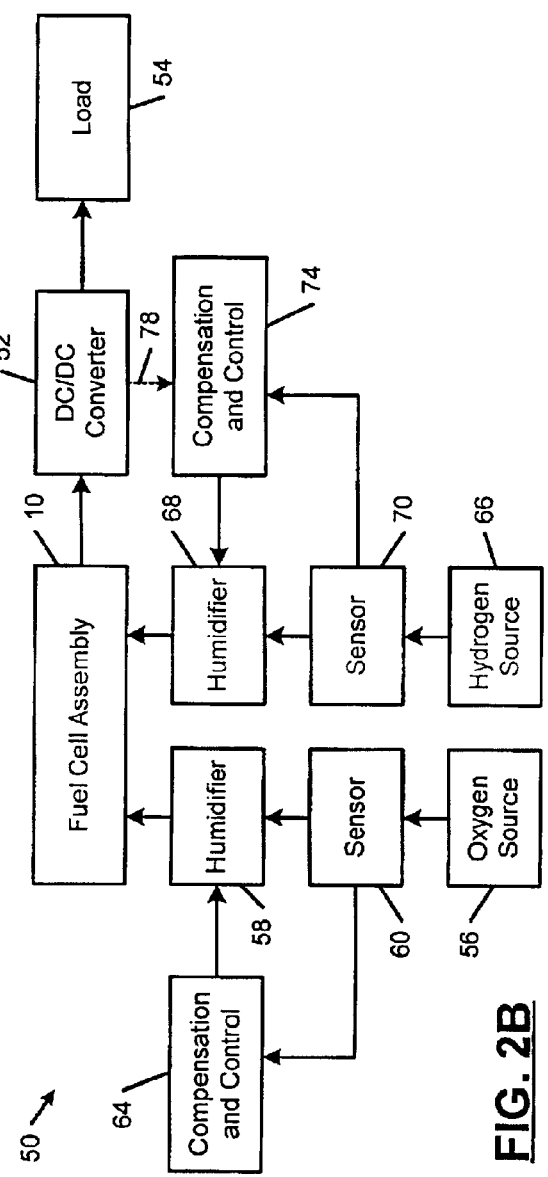

RELATIVE HUMIDITY SENSOR WITH COMPENSATION FOR CHANGES IN PRESSURE AND GAS COMPOSITION

FIELD OF THE INVENTION

The present invention relates to a fuel cell and, more particularly, to a system and method for compensating a relative humidity signal output by a relative humidity sensor of a fuel cell for variations in pressure, temperature and gas composition.

BACKGROUND OF THE INVENTION

Fuel cells are increasingly being used as a power source in a wide variety of different applications. Fuel cells have also been proposed for use in electrical vehicular power plants to replace internal combustion engines. A solid-polymer-electrolyte fuel cell includes a membrane that is sandwiched between an anode and a cathode. To produce electricity through an electrochemical reaction, hydrogen ($H_2$) is supplied to the anode and air or oxygen ($O_2$) is supplied to the cathode.

In a first half-cell reaction, dissociation of the hydrogen ($H_2$) at the anode generates hydrogen protons ($H^+$) and electrons ($e^-$). The membrane is proton conductive and dielectric. As a result, the protons are transported through the membrane while the electrons flow through an electrical load that is connected across the electrodes. In a second half-cell reaction, oxygen ($O_2$) at the cathode reacts with protons ($H^+$), and electrons ($e^-$) are taken up to form water ($H_2O$).

To operate efficiently and to produce a maximum amount of electricity, the fuel cell must be properly humidified. To achieve the proper humidity range, the hydrogen stream and/or the air stream are typically humidified by one of several methods known in the art. Conventional humidity control methods generally fail to sufficiently control the humidity of the hydrogen and air streams to the fuel cell. Providing too much humidity to the fuel cell blocks the reacting gases from accessing the catalyst thereby impeding the electrochemical reaction between the hydrogen and air and reducing the production of electricity. Providing too little humidity to the fuel cell restricts or limits the proton transportation required for reaction within the fuel cell.

In U.S. patent applications Ser. No. 09/491,308 now 6,376,111, entitled "System and Method for Controlling the Humidity Level of a Fuel Cell", which is hereby incorporated by reference, a controller 44 utilizes feedback to control the humidity of the fuel cell assembly. The resistance of the fuel cell assembly (as measured across the DC/DC converter) is used to control the humidity of the fuel cell assembly.

Relative humidity sensor readings are needed at the inlet of the anode and the cathode so that the humidity level can be accurately determined and controlled. Commercially available relative humidity sensors are typically calibrated for operation in a specific medium such as air, for a particular temperature range, and for a particular pressure range such as atmospheric pressure. When these relative humidity sensors are placed in pressurized air, reformate and/or hydrogen streams of a fuel cell, the resulting measurement of the relative humidity is no longer accurate. Failure to properly control the relative humidity of the fuel cell leads to the problems described above. The commercially available relative humidity sensors have not been calibrated to handle variations in temperature, pressure and gas composition that are likely to be encountered in fuel cells. Development of sensors that are accurate despite the variations in operating conditions has been difficult and expensive. The cost of the humidity sensor becomes more important when the fuel cells are used to power a motor vehicle. One major obstacle limiting the commercial feasibility of fuel cells in motor vehicles is cost.

SUMMARY OF THE INVENTION

A system for sensing the humidity level of a fuel cell according to the invention includes a humidity sensor that senses the relative humidity of a gas stream and generates a relative humidity signal. A first sensor senses pressure or temperature of the gas stream and generates a temperature signal or a pressure signal. A compensator is connected to the humidity sensor and the first sensor and generates a compensated relative humidity signal based on the relative humidity signal and the temperature signal or the pressure signal.

According to other features of the invention, the system further includes a humidifier. A controller is connected to the compensator and the humidifier. The controller increases the relative humidity of the gas stream based on the compensated relative humidity signal.

According to still other features of the invention, the gas stream is provided by a reformate source or a hydrogen source to an anode of the fuel cell. Alternately, the gas stream is provided by an air source or an oxygen source to a cathode of the fuel cell.

In other features of the invention, the compensator includes memory containing look-up tables and/or mathematical formulas that are used to determine the compensated relative humidity signal.

In still other features of the invention, a gas composition sensor senses the concentration of a first gas in the gas stream and generates a first gas concentration signal. The compensator is connected to the gas composition sensor. The compensated relative humidity signal is based on the relative humidity signal, the temperature signal or the pressure signal, and the first gas composition signal.

Still other objects, features and advantages will be readily apparent to skilled artisans from the specification, the claims and the drawings.

BRIEF DESCRIPTION OF THE DRAWINGS

The various features, advantages and other uses of the present invention will become more apparent by referring to the following description and the drawings in which:

FIGS. 2A and 2B are schematic block diagrams of systems for controlling the humidity level of a fuel cell in accordance with the present invention.

DETAILED DESCRIPTION OF THE PREFERRED EMBODIMENT

The ensuing detailed description provides preferred exemplary embodiments only and is not intended to limit the scope, applicability or configuration of the present invention. Rather, the ensuing detailed description of the preferred exemplary embodiments will provide those skilled in the art with an enabling description for implementing the preferred exemplary embodiments of the present invention. It being understood that various changes may be made in the function and arrangement of the elements without departing from the spirit and scope of the invention as set forth in the appended claims.

The relative humidity sensor according to the present invention employs a conventional humidity sensor, a temperature sensor, one or more gas composition sensors, and/or a pressure sensor. The output of the humidity sensor is compensated to reflect the gas composition, the temperature and/or the pressure of the gas stream. The relative humidity compensation is preferably accomplished using lookup tables or by calculating a corrected output signal using one or more known mathematical functions. The relative humidity compensation is based upon the sensed gas composition, the sensed temperature and/or the sensed pressure. As a result of the compensation, the present invention allows the use of the conventional relative humidity sensor in applications with transient conditions. In addition, the relative humidity sensor according to the present invention can be manufactured in a small, efficient and cost effective package.

Figure 1:
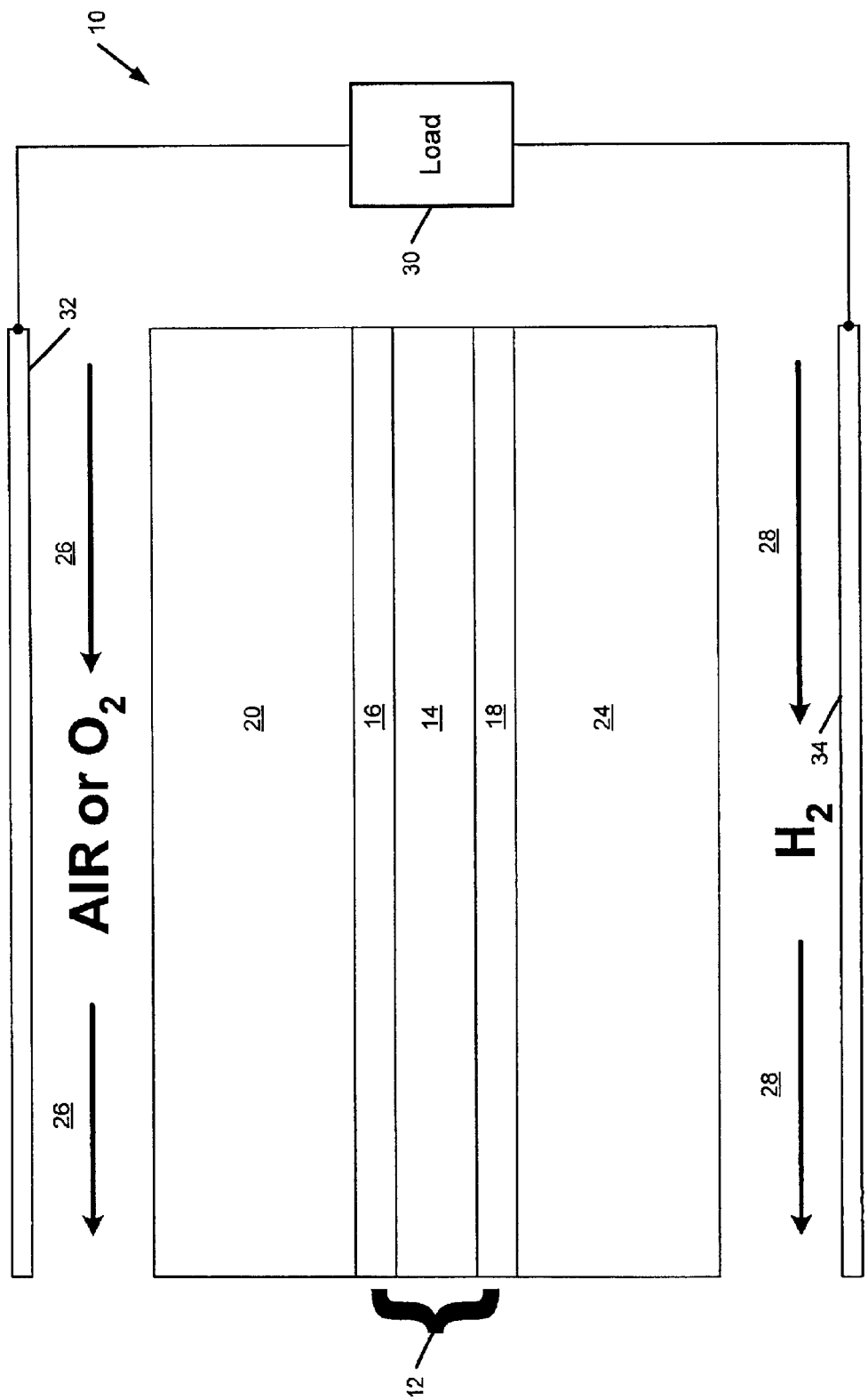
FIG. 1 illustrates a cross-section of a membrane electrode assembly of a fuel cell assembly.

Referring now to FIG. 1, a cross-section of a fuel cell assembly 10 that includes a membrane electrode assembly (MEA) 12 is shown. Preferably, the membrane electrode assembly is a proton exchange membrane (PEM). The membrane electrode assembly 12 includes a membrane 14, a cathode 16, and an anode 18. The membrane 14 is sandwiched between the cathode 16 and the anode 18.

A cathode diffusion medium 20 is layered adjacent to the cathode 16 opposite the membrane 14. An anode diffusion medium 24 is layered adjacent to the anode 18 opposite the membrane 14. The fuel cell assembly 10 further includes a cathode flow channel 26 and anode flow channel 28. The cathode flow channel 26 receives and directs oxygen or air ($O_2$) from a source to the cathode diffusion medium 20. The anode flow channel 28 receives and directs hydrogen ($H_2$) from a source to the anode diffusion medium 24.

In the fuel cell assembly 10, the membrane 14 is a cation permeable, proton conductive membrane having $H^+$ ions as the mobile ion. The fuel gas is hydrogen ($H_2$) and the oxidant is oxygen or air ($O_2$). The overall cell reaction is the oxidation of hydrogen to water and the respective reactions at the anode 18 and the cathode 16 are as follows:

$H_2 = 2H^+ + 2e^-$

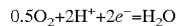

$0.5O_2 + 2H^+ + 2e^- = H_2O$

Since hydrogen is used as the fuel gas, the product of the overall cell reaction is water. Typically, the water that is produced is rejected at the cathode 16, which is a porous electrode including an electrocatalyst layer on the oxygen side. The water may be collected as it is formed and carried away from the MEA 12 of the fuel cell assembly 10 in any conventional manner.

The cell reaction produces a proton exchange in a direction from the anode diffusion medium 24 towards the cathode diffusion medium 20. In this manner, the fuel cell assembly 10 produces electricity. An electrical load 30 is electrically connected across the MEA 12 a first plate 32 and a second plate 34 to receive the electricity. The plates 32 and/or 34 are bipolar plates if a fuel cell is adjacent to the respective plate 32 or 34 or end plates if a fuel cell is not adjacent thereto.

To operate efficiently and to produce the maximum amount of electricity, the fuel cell assembly 10 should be properly humidified. Typically, one or both of the air stream supplied to the cathode flow channel 26 and the hydrogen stream supplied to the anode flow channel 28 are humidified by one of several ways known in the art. In a common approach, the anode gases and/or cathode gases are directed to a membrane humidifier before they are directed to the fuel cell. The humidifier may be either external to the fuel cell or it may comprise a section within the fuel cell stack. In another approach, the fuel cell can also be humidified via use of water wicking materials, as disclosed in U.S. Pat. Nos. 5,935,725 and 5,952,119, which are hereby incorporated by reference, that direct water from a reservoir to the MEA 12. Alternatively, steam or a mist of water ($H_2O$) may be injected into both the cathode stream and the anode stream to humidify these streams upstream of or within the fuel cell stack. In yet another approach, an oxygen stream may be injected in the hydrogen stream upstream of the anode flow channel 28 to react a small amount of $H_2$ to produce $H_2O$ to humidify the hydrogen stream.

Referring now to FIG. 2A, a fuel cell system 50 is illustrated and includes the fuel cell assembly 10. An output of the fuel cell assembly 10 is connected to a DC/DC converter 52 that is connected to a load 54. An oxygen source 56 is connected to a first humidifier 58. A first sensor or a group of sensors 60 generates a temperature signal, a pressure signal, and/or a gas composition signal of one or more components of the gas stream flowing to the cathode of the fuel cell assembly 10. A first compensation and control circuit 64 is connected to one or more outputs of the first sensor 60 and receives the temperature signal, the pressure signal, and/or the gas composition signal therefrom.

A hydrogen source 66 is connected to a second humidifier 68. A second sensor or a group of sensors 70 generates a temperature signal, a pressure signal, and/or a gas composition signal of one or more components of the gas stream flowing to the anode of the fuel cell assembly 10. The relative humidity measurement may be impacted by variations in the concentration of $CO$, $CO_2$, and $N_2$. A second compensation and control circuit 74 is connected to one or more outputs of the second sensor 70 and receives the temperature signal, the pressure signal, and/or the gas composition signal therefrom. One or both of the compensation and control circuits 64 and 74 may be connected to an output of the DC/DC converter 52 as is indicated by dotted lines 78.

Referring now to FIG. 2B, the relative position of the first and second sensors can be varied. Reference numbers from FIG. 2A are employed in FIG. 2B where appropriate to denote similar elements. Skilled artisans can appreciate that the relative position of the sensors 60 and 70 can be varied in a number of different ways. For example, in FIG. 2B, the sensors 60 and 70 are positioned between the output of the oxygen and hydrogen sources 56 and 66 and the first and second humidifiers 58 and 68. While the output of the oxygen source 56 is shown passing through the sensors 60, any suitable arrangement is contemplated. For example, the temperature, pressure and/or gas composition measurements are typically performed using a sensor that is inserted into a bore of a conduit or pipe that carries the air, oxygen, reformate, or hydrogen.

Figure 3:
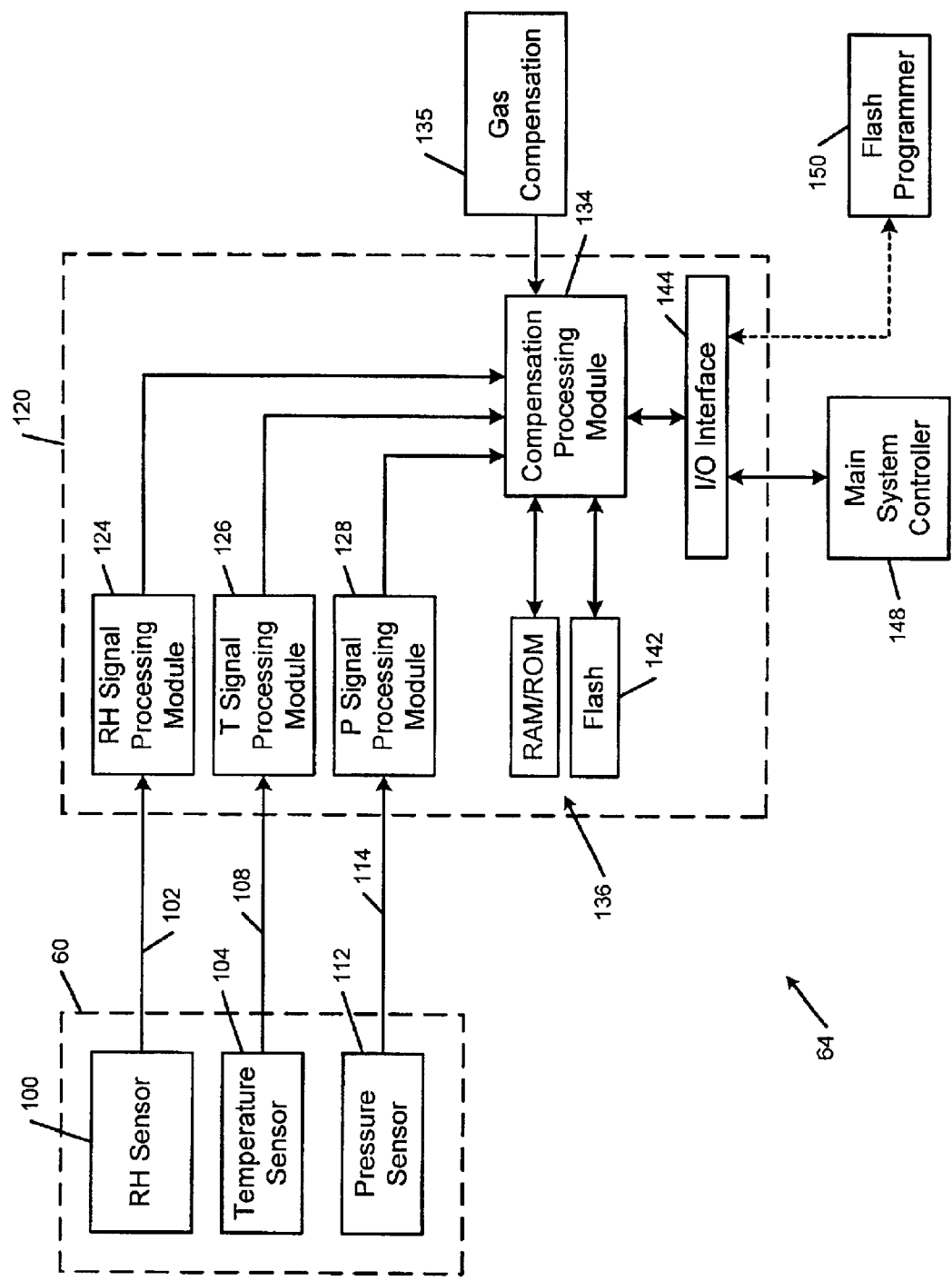
FIG. 3 is a schematic block diagram of a compensated humidity sensor and control of the fuel cell in FIG. 2.

Referring now to FIG. 3, the first sensor or group of sensors 60 includes a relative humidity sensor 100 that generates a relative humidity signal 102, a temperature sensor 104 that generates a temperature signal 108, and/or a pressure sensor 112 that generates a pressure signal 114. A relative humidity compensating circuit 120 includes a relative humidity signal processing module 124, a temperature signal processing module 126, and/or a pressure signal processing module 128. Outputs of all of the modules 124, 126 and 128 are input to a compensation processing module 134. One or more gas composition sensors 135 provide one or more gas composition signals that relate to the presence of a component in the gas stream to the compensation processing module 134 so that the composition of the gas can be determined.

The compensation processing module 134 is connected to memory 136 that preferably includes read-only memory (ROM), random access memory (RAM) 140, flash memory 142 or any other suitable electronic memory. The compensation processing module 134 is connected to an input/output (I/O) interface 144. A main system controller 148 is connected to the I/O interface 144. A flash programmer 150 is removably connected to the I/O interface 144. The compensation processing module 134 factors the relative humidity signal 102, the temperature signal and/or the pressure signal 114 using a stored lookup table, mathematical formulas, combinations thereof, or other suitable means to adjust the relative humidity signal based upon the temperature, the gas composition and the pressure.

Relative humidity is impacted by temperature, pressure and the constituents in the gas stream. The following equations set forth the relationship:

$$(RH/100)=P_w/P_s=(\eta_{fw}P_{TOTAL})/P_s$$

where:
$P_w$=mole fraction of water times total pressure
$P_s$=saturated pressure of stream
$\eta_{fw}$=mole fraction of water
$\eta_{fw}=\eta_w/\eta_{TOTAL}$
$\eta_{fw}$=(mole rate water)/(total mole rate)

Therefore, using the relationship set forth above, the relative humidity output of the conventional sensor can be adjusted for variations in total pressure of the stream, the temperature of the stream, and/or for variations in the gas compositions. As such, the voltage output of the sensor is adjusted accordingly to provide the correct output. By relying on conventional sensors that are compensated, the cost of the relative humidity sensor can be reduced without a corresponding loss in accuracy.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. A system for sensing the relative humidity of a fuel cell, comprising;
    a humidity sensor that senses the relative humidity of a gas stream supplied to an electrode of said fuel cell and that generates a relative humidity signal;
    a first sensor that senses at least one of pressure and temperature of said gas stream and generates at least one of a temperature signal and a pressure signal; and
    a compensator that is connected to said humidity sensor and said first sensor and that generates a compensated relative humidity signal based on said relative humidity signal and said at least one of said temperature signal and said pressure signal; and
    wherein said gas stream is provided by one of a reformate source and a hydrogen source to said electrode which is an anode of said fuel cell.

2. A system for sensing the relative humidity of a fuel cell comprising:
    a humidity sensor that senses the relative humidity of a gas stream supplied to an electrode of said fuel cell and that generates a relative humidity signal;
    a first sensor that senses at least one of pressure and temperature of said gas stream and generates at least one of a temperature signal and a pressure signal; and
    a compensator that is connected to said humidity sensor and said first sensor and that generates a compensated relative humidity signal based on said relative humidity signal and said at least one of said temperature signal and said pressure signal; and
    a gas composition sensor for sensing a concentration of a first gas in said gas stream and for generating a first gas concentration signal.

3. The system of claim 2 wherein said gas stream is provided by one of an air source and an oxygen source to said electrode which is a cathode of said fuel cell.

4. The system of claim 2 wherein said compensator is connected to said gas composition sensor and wherein said compensated relative humidity signal is based on said relative humidity signal, said at least one of said temperature and said pressure signal, and said first gas composition signal.

5. The system of claim 2 wherein said first gas is one of nitrogen, carbon monoxide, and carbon dioxide.

6. A system for sensing the relative humidity of a fuel cell, comprising:
    a humidity sensor that senses the relative humidity of a gas stream and generates a humidity signal;
    a gas composition sensor for sensing a concentration of a first gas in said gas stream and for generating a first gas composition signal; and
    a compensator that is connected to said humidity sensor and said temperature sensor and that generates a compensated relative humidity signal based on said relative humidity signal and said first gas composition signal.

7. The system of claim 6 further comprising:
    a pressure sensor that generates a pressure signal that is based on a pressure of said gas stream.

8. The system of claim 7 wherein said compensator is connected to said pressure sensor and wherein said compensated relative humidity signal is based on said relative humidity signal, said first gas compensation signal and said pressure signal.

9. The system of claim 6 further comprising:
    a humidifier; and
    a controller connected to said compensation circuit and said humidifier for increasing said relative humidity of said gas stream based on said compensated relative humidity signal.

10. The system of claim 6 wherein said gas stream is provided by one of a reformate source and a hydrogen source to an anode of said fuel cell.

11. The system of claim 6 wherein said gas stream is provided by one of an air source and an oxygen source to a cathode of said fuel cell.

12. The system of claim 6 wherein said compensator includes memory containing look-up tables that are used to generate said compensated relative humidity signal.

13. The system of claim 6 wherein said compensator employs mathematical formulas that are used to generate said compensated relative humidity signal.

14. The system of claim 6 further comprising:
a temperature sensor that senses a temperature of said gas stream and generates a temperature signal.

15. The system of claim 14 wherein said compensator is connected to said temperature sensor and wherein said compensated relative humidity signal is based on said relative humidity signal, said first gas compensation signal and said temperature signal.

16. The system of claim 6 wherein said first gas is one of nitrogen, carbon monoxide, and carbon dioxide.

17. A system for sensing the relative humidity of a fuel cell, comprising:
a humidity sensor that senses the relative humidity of a hydrogen-containing gas stream and generates a relative humidity signal;
a first sensor that senses at least one of pressure and temperature of said gas stream and generates at least one of a temperature signal and a pressure signal; and
a compensator that is connected to said humidity sensor and said first sensor and that generates a compensated relative humidity signal based on said relative humidity signal and said at least one of said temperature signal and said pressure signal.

18. The system of claim 17 further comprising:
a humidifier; and
a controller connected to said compensator and said humidifier for increasing said relative humidity of said gas stream based on said compensated relative humidity signal.

19. The system of claim 17 wherein said compensator includes memory containing look-up tables.

20. The system of claim 17 wherein said compensator employs mathematical formulas to determine said compensated relative humidity signal.

* * * * *